United States Patent
Delaney et al.

(10) Patent No.: US 11,890,424 B2
(45) Date of Patent: Feb. 6, 2024

(54) AUGMENTED REALITY ENABLED MOTION SICKNESS REDUCTION

(71) Applicant: INTERNATIONAL BUSINESS MACHINES CORPORATION, Armonk, NY (US)

(72) Inventors: Mark Delaney, Raleigh, NC (US); Robert Huntington Grant, Atlanta, GA (US); Zachary A. Silverstein, Austin, TX (US); Paul Bergen, Hillsborough, NJ (US)

(73) Assignee: International Business Machines Corporation, Armonk, NY (US)

(*) Notice: Subject to any disclaimer, the term of this patent is extended or adjusted under 35 U.S.C. 154(b) by 678 days.

(21) Appl. No.: 16/511,812

(22) Filed: Jul. 15, 2019

(65) Prior Publication Data

US 2021/0016052 A1 Jan. 21, 2021

(51) Int. Cl.
  *A61M 21/02* (2006.01)
  *G02B 27/00* (2006.01)
  *A61M 21/00* (2006.01)

(52) U.S. Cl.
  CPC ......... *A61M 21/02* (2013.01); *G02B 27/0093* (2013.01); *A61M 2021/0044* (2013.01)

(58) Field of Classification Search
  CPC .... A61M 21/00; A61M 21/02; G02B 27/0093
  See application file for complete search history.

(56) References Cited

U.S. PATENT DOCUMENTS

| | | |
|---|---|---|
| 5,966,680 A | 10/1999 | Butnaru |
| 6,497,649 B2 | 12/2002 | Parker et al. |
| 7,474,335 B2 | 1/2009 | Basson et al. |
| 8,690,750 B2 | 4/2014 | Krueger |

(Continued)

OTHER PUBLICATIONS

Mell et al., "The NIST Definition of Cloud Computing", Recommendations of the National Institute of Standards and Technology, NIST Special Publication 800-145, Sep. 2011, 7 pages.

(Continued)

*Primary Examiner* — Christine H Matthews
(74) *Attorney, Agent, or Firm* — Anthony Curro

(57) ABSTRACT

A method, computer system, and a computer program product for reducing a motion sickness episode experienced by a user. The present invention may include detecting a triggering environment associated with the user, wherein detection of such environment utilizes a plurality of analyzed data associated with a plurality of sensors. The present invention may then include extracting a piece of data associated with the environment in further association with the motion sickness episode experienced by the user. The present invention may also generate one or more responses based on the extracted piece of data associated with the motion sickness episode. The present invention may then implement the generated one or more responses associated with the motion sickness episode by utilizing an augmented reality (AR) device. The present invention may further include providing a piece of feedback associated with the generated one or more responses associated with the motion sickness episode.

20 Claims, 5 Drawing Sheets

(56) References Cited

U.S. PATENT DOCUMENTS

| 10,108,018 | B2 | 10/2018 | Takahashi et al. | |
|---|---|---|---|---|
| 2007/0034212 | A1 | 2/2007 | Brendley et al. | |
| 2015/0363976 | A1* | 12/2015 | Henson | H04N 13/344 345/419 |
| 2018/0089901 | A1 | 3/2018 | Rober et al. | |
| 2018/0184014 | A1 | 6/2018 | Goldstein | |
| 2018/0260026 | A1* | 9/2018 | Drake | G02B 27/017 |

OTHER PUBLICATIONS

Anonymous, "Motion Sickness Mitigation Using VR/AR Devices", Technical Disclosure Commons, Defensive Publications Series, Dec. 11, 2018, 9 pages.

Kitazaki et al., "Control of Eye-movement to Decrease VE-sickness", VRST 2006, Nov. 1-3, 2006, pp. 350-355.

Nie et al., "[Poster] Prevention of Visually Induced Motion Sickness Based on Dynamic Real-time Content-aware Non-Salient Area Blurring", 2017 IEEE International Symposium on Mixed and Augmented Reality Adjunct Proceedings, pp. 75-78.

Bonato et al., Abstract for "Display color affects motion sickness symptoms in an optokinetic drum", Aviat. Space Environ. Med., Apr. 2004, vol. 75, No. 4, pp. 306-311.

Brainard et al., "Prevention and Treatment of Motion Sickness", Downloaded from the American Family Physician Website at www.aafp.org/afp, 2014, 6 pages.

IBM, "Use computer vision to detect and track moving objects in video", Published on May 11, 2018, 5 pages, https://developer.ibm.com/code/2018/05/11/using-computer-vision-to-detect-and-track-moving-objects-in-video/.

Tucker, "This Inventor May Have Cured Motion Sickness without Drugs. And That Could Mean a Lot to the US Military", Nov. 20, 2018, 8 pages, https://www.defenseone.com/technology/2018/11/inventor-may-have-cur/.

ENT Health, "Benign Paroxysmal Positional Vertigo (BPPV)", printed on Jul. 15, 2019, 6 pages.

Erskine et al., "Motion Sickness" Centers for Disease Control and Prevention, Chapter 2, The Pretravel Consultation, Self-Treatable Conditions, 2018, 3 pages.

Cozman, "Horizon Detection", printed on Jul. 15, 2019, 1 page, http://www.cs.cmu.edu/%7Eviper/Papers/WACV96/node5.html.

Jokerst et al., Abstract for "Slow deep breathing prevents the development of Tachygastria and symptoms of motion sickness", Aviat. Space Environ, Med., Dec. 1999, vol. 70, No. 12, pp. 1189-1192.

Ku, "Motion Sickness in VR", UX Planet, Nov. 29, 2018, 5 pages.

Schechter, "What is Markerless Augmented Reality? | AR Bites", Marxent®, May 9, 2014, 4 pages.

Tan, "Uber is going to make care sickness a thing of the past-especially in driverless cars", Mashable, Nov. 21, 2017, 7 pages.

Van Kaick et al., "Automatic Classification of Outdoor Images by Region Matching", The 3rd Canadian Conference on Computer and Robot Vision, Jul. 2006, 8 pages.

\* cited by examiner

AUGMENTED REALITY ENABLED MOTION SICKNESS REDUCTION

BACKGROUND

The present invention relates generally to the field of computing, and more particularly to augmented reality together with healthcare.

Motion sickness is a complex syndrome that affects millions of people in a variety of ways, making motion sickness hard to manage. Traditionally, methods to reduce the motion sickness may either fail to work in multiple environments or fail to be helpful.

SUMMARY

Embodiment of the present invention disclose a method, computer system, and a computer program product for reducing a motion sickness episode experienced by a user. The present invention may include detecting a triggering environment associated with the user, wherein detection of a triggering environment utilizes a plurality of analyzed data associated with a plurality of sensors. The present invention may then include extracting a piece of data associated with the detected triggering environment in further association with the motion sickness episode experienced by the user. The present invention may also generate one or more responses associated with the motion sickness episode experienced by the user based on the extracted piece of data associated with the motion sickness episode. The present invention may then implement the generated one or more responses associated with the motion sickness episode by utilizing an augmented reality (AR) device. The present invention may further include providing a piece of feedback associated with the generated one or more responses associated with the motion sickness episode.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
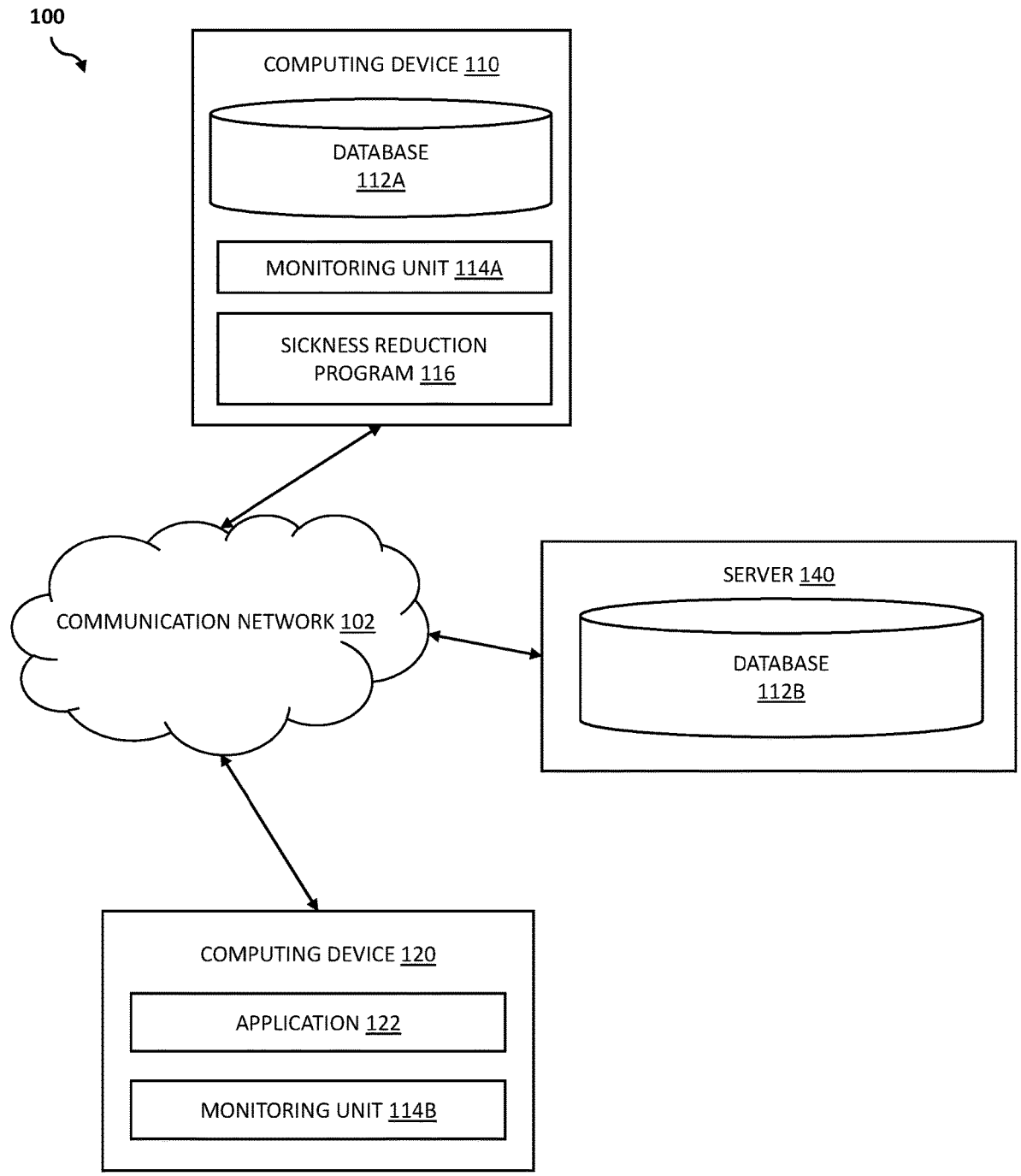
FIG. 1 illustrates a networked computer environment, sickness reduction system, according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed concurrently, substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product for reducing a motion sickness episode experienced by a user. As such, the present embodiment has the capacity to improve the technical field of healthcare by utilizing augmented reality (AR) to reduce an episode of motion sickness experienced by the user. More specifically, the present invention first may detect a triggering environment associated with the user. Such detection of the environment may utilize, in embodiments, a plurality of analyzed data obtained from a combination of sensors. Further, the present invention may extract a piece of data from the environment associated with the motion sickness episode experienced by the user. Additionally, the present invention may generate a response based on the environmental data. Such a response may be implemented utilizing augmented reality. Subsequent to implementation, feedback may be transferred to the user regarding the one or more generated responses associated with the experienced motion sickness of the user.

As previously described, motion sickness is a complex syndrome that affects millions of people in a variety of ways, making motion sickness hard to manage. Traditionally, methods to reduce the motion sickness may either fail to work in multiple environments or fail to be helpful. Traditional methods, however, have yet to explore generating responses to identified causes in combination with user history under a modified visual environment.

Therefore, it may be advantageous to, among other things, implement a technique to reduce motion sickness that may introduce varying levels of stimuli using an augmented reality (AR) device, relative to a user's sensitivity to the stimuli, ability to adapt to the stimuli, and time factor of the user's response to the motion sickness. Adaptations of stimuli may include obfuscation, addition, or removal or surrounding stimuli, adaptation of visual field color spectrums, and reduction of pitching and rolling of the identified horizon.

According to at least one embodiment, a sickness reduction program may activate a motion sickness module. In the present embodiment, the sickness reduction program may be activated manually via a user starting a program or tutorial on their mobile device (e.g., opening an application). The sickness reduction program may, in other embodiments, be activated automatically via AR device detection of biometric information from Internet of Things (IoT) devices in addition to sensors and context. In such embodiments, biometric information may be obtained from biometric sensors (e.g., a smart watch to detect a heartbeat or an AR headset to detect eye gaze and blink rate). The sickness reduction program may also obtain information via auditory capture of user speech (e.g., the User says "I think I'm going to be sick") as well as context captured information in conjunction with historically known motion sickness engaging events (e.g., calendar note says flight or input reveals the user is on a boat).

According to at least one embodiment, the sickness reduction program may detect a current outstanding context. Outstanding context (e.g., the user's environment) may include detecting the horizon in the user's visual field by comparing the skyline to the groundline, capturing non-relative static positioned objects, and classifying the environment in which the user is located. Such detection, capture, or classification of elements may utilize the augmented reality capabilities of the program device 110. Contextual elements may be obtained via image recognition, image processing, image recommendation, or manual identification (e.g., through a trained machine learning algorithm).

According to at least one embodiment, the sickness reduction program may detect whether the user has a user profile history (i.e., profile history, user profile, profile) in the system that is being utilized. In the present embodiment, the sickness reduction program may analyze a local database to search for a profile associated with the user. In other embodiments, the sickness reduction program may analyze a remote database to search for a profile associated with the user. Profile history of a user may include name, age, height, weight, previously used techniques that were effective, previously used techniques that were ineffective, previously identified triggering environments (e.g., a boat), specific patterns or color overlays that were effective (e.g., 30% increase of the blue spectrum in the visual field), specific objects for injection for a focal point that were effective (e.g., a lighthouse), the most effective degree of amelioration, the context in which each technique was used, as well as the average length of time of the motion sickness event (i.e., motion sickness episode) for such user.

According to at least one embodiment, the sickness reduction program, having located a user profile history, may return the specific ameliorative techniques that are most effective for the user (i.e. specific techniques, personalized ameliorative techniques). Specific techniques may be extracted, in such an embodiment, from communication and data transfers with the database in which the user profile history was found. In the present embodiment, the database may either be local to the user's device or remotely found (e.g., on a server).

According to at least one embodiment, the sickness reduction program, having failed to locate a user profile history, may, in turn, return generic ameliorative techniques (i.e. generic techniques) that are coded into the sickness reduction program. In this embodiment, such generic techniques may be captured via research of effective motion sickness reduction techniques. In the present embodiment, research may be collected from hardcoded medical studies, trusted Internet sources, medical journals, patient records, and any other reliable sources, including authoritative and/or relevant sources, that may provide information about motion sickness reduction to the sickness reduction program. Predefined ameliorative generic techniques may include AR generation of a focal point object, the use of specific color schemes in the user's visual field, the modification of sights and sounds in the user's visual field, the obfuscation of objects of a specific size, type, and/or shape, the prompting of the user to modify their current position, the simplifying of sensory input, the reduction of pitching and rolling of the identified horizon, the alteration of luminescence and temperature warmth, the detection and guidance of user breathing patterns, the modification of the current state of the computing device of the user itself (e.g., vibrations of the headset, sounds produced by the headset), as well as the blockage of one or more non-static items moving non-relative to the user associated with the AR device. In other embodiments, generic ameliorative techniques may be obtained by the sickness reduction program via a ranking of most popular ameliorative techniques crowdsourced from a knowledge base in which the ranking may be based upon the average motion sickness time reduction data. In further embodiments, the sickness reduction program may obtain generic ameliorative techniques using a combination of crowdsourced knowledge as well as researched data.

In at least one embodiment, the sickness reduction program may implement the general techniques obtained from the sickness reduction program. In the present embodiment, the sickness reduction program may run the hardcoded program instructions found in the local or remote database to carry out the general technique (e.g., run the code to change the user's visual field from a 10% blue spectrum overlap to a 30% blue spectrum overlay). In embodiments, the sickness reduction program may utilize AR-enabled devices capable of applying such general techniques (e.g., an AR headset, glasses capable of AR).

In at least one embodiment, the sickness reduction program may capture the length of time that the user experienced the motion sickness. In the present embodiment, the sickness reduction program may utilize automatic capturing via biometric scanning. Biometric scanning may utilize IoT devices in addition to sensors to capture biometric data. In further embodiments, the sickness reduction program may utilize manual capturing where the user provides feedback to the sickness reduction program. In such embodiments, the sickness reduction program may obtain the status of the user via manual input. Manual input may be obtained either locally (e.g., the press of a button on the device that was used to apply the techniques) or remotely (e.g., from a mobile application on a mobile device of the user).

In at least one embodiment, the sickness reduction program may update the user's profile to include the techniques used to reduce the motion sickness of the user. In such embodiment, the sickness reduction program may analyze the length of time of the motion sickness event, previously obtained, and will determine how effective the technique was in comparison to other techniques previously used in which such previously used techniques may be found in the user's profile. In such embodiments, if a user history profile was not found, the sickness reduction program may create a profile and store the used technique and the associated components in a database.

In at least one embodiment, the sickness reduction program may update the crowdsourced knowledge base to include the most previously used technique, the associated contextual cues as well as the effectiveness of the technique. The sickness reduction program may communicate to the database locally in which the database is on the device, or via a network communication, or the database is on a server or a remote device.

FIG. 1 depicts a sickness reduction system 100, in accordance with embodiments of the present invention. In the example embodiment, the sickness reduction system 100 includes a program device 110, a user input device 120, (i.e., computer device 120, computing device 120, program device 120) and a server 140, interconnected via a communication network 102. While, in the example embodiment, programming and data of the present invention are stored and accessed remotely across several servers (e.g. the server 140) via the communication network 102, in other embodiments, programming and data of the present invention may be stored locally on as few as one physical computing device or amongst other computing devices than those depicted.

In the example embodiment, the communication network 102 is a communication channel capable of transferring data between connected devices. In the example embodiment the communication network 102 is the Internet, representing a worldwide collection of networks and gateways to support communications between devices connected to the Internet.

Moreover, the communication network 102 may include, for example, wire, wireless, or fiber optic connections which may be implemented as an intranet network, a wide area network (WAN), a local area network (LAN), a telecommunication network, a wireless network, a public switched network, a satellite network, or a combination thereof. In general, the communication network 102 can be any combination of connections and protocols that will support communications between the program device 110, the user input device 120, and the server 140. It should be appreciated that FIG. 1 provides only an illustration of one implementation and does not imply any limitations with regard to the environments in which different embodiments may be implemented. Many modifications to the depicted environments may be made based on design and implementation requirements.

In the example embodiment, the program device 110 includes a database 112A, a monitoring unit 114A, and a sickness reduction program 116 and may be a laptop computer, a netbook computer, a personal computer (PC), a desktop computer, a server, a personal digital assistant (PDA), a rotary phone, a touchtone phone, a smart phone, a mobile phone, an augmented reality device, a virtual reality device, a thin client, a wearable device, or any other electronic device or computing system capable of receiving and sending data to and from other computing devices. While, in the example embodiment, the program device 110 is shown as a single device, in other embodiments, the program device 110 may be comprised of a cluster or plurality of computing devices, working together or working separately. In various embodiments, the sickness reduction system 100 may include one or more of the program device 110, wherein a user of the program device 110 may send data to the user input device 120, or the server 140.

In the example embodiment, the database 112A is a collection of files including but not limited to, hypertext markup language (i.e., HTML) files, cascading style sheets (i.e., CSS) files, extensible markup language (i.e., XML) files, and JavaScript files. In general, the database 112A is comprised of user specific historical and current profile information. In the example embodiment, the database 112A is locally stored on the program device 110 and may not require any network communication procedures to access information stored in the database 112A. In other embodiments, the database 112A may be stored remotely on any other combination of computing devices or servers, wherein the computing devices and servers may work independently or dependently with communications via communication network 102.

In the example embodiment, the monitoring unit 114A (and the monitoring unit 114B of the user input device 120) may be comprised of a combination of devices, subsystems, or modules wherein the combination of these devices measures events or detects changes in the environment in which the device is being used. In embodiments, the monitoring unit 114A (114B) may communicate with other devices in the sickness reduction system 100 to transfer data and command programs to run. In the example embodiment, the data collected from the monitoring unit 114A (114B) may be stored locally on the program device 110. In other embodiments, the data collected may be stored remotely and accessed via communications network 102. In the example embodiment, the monitoring unit 114A (114B) may be a heart rate monitor (i.e., HRM) used to detect heartbeat, an eye tracking device used to detect eye gaze, blink rate detection, or a level of wakefulness, an environmental sensor to detect contextually triggering events, an accelerometer or gyroscope to detect motion, a 360° camera to detect environmental changes, a microphone to detect voice commands, a monitor of the median nerve to detect a level of nausea, a blood pressure monitor to monitor blood pressure, or a respiration monitor to detect breathing patterns. The monitoring unit 114A (114B) may be comprised of a cluster or plurality of computing devices, working together, or working separately.

In the example embodiment, the sickness reduction program 116 is a software program that supports communications between one or more users of the program device 110, the user input device 120 or the server 140. In the example embodiment, a user accesses the sickness reduction program 116 by navigation and communication of the user input device 120 via the communication network 102. In other embodiments, the sickness reduction program 116 can be accessed by transferred data from the monitoring unit 114A. In general, the sickness reduction program 116 is capable of applying ameliorations wherein such ameliorations may comprise generic techniques to reduce motion sickness in addition to techniques that have proved effective to the specific user in prior circumstances and situations. Additionally, the sickness reduction program 116 is capable of generating a fixed point on the horizon on the augmented reality device and blocking/obfuscating non-static items moving non-relative to a user associated with the augmented reality device. The sickness reduction program 116 may utilize analysis techniques to interpret and understand data from the monitoring unit 114A, 114B.

In the example embodiment, the user input device 120 includes an application 122 and a monitoring unit 114B and may be a laptop computer, a netbook computer, a personal computer (PC), a desktop computer, a server, a personal digital assistant (PDA), a rotary phone, a touchtone phone, a smart phone, a mobile phone, an augmented reality device, a virtual reality device, a thin client, a wearable device, or any other electronic device or computing system capable of receiving and sending data to and from other computing devices, running a program, accessing a network, and accessing a database. While, in the example embodiment, the computing device is shown as a single device, in other embodiments, the program device 110 may be comprised of a cluster or plurality of computing devices, working together or working separately. The user input device 120 may communicate with the program device 110, and the server 140 via the communications network 102. In general, the computer device 120 is capable of manual user input that can be communicated to the program device 110 and the server 140 via the communication network 102.

The application 122, in the example embodiment, is a software program that supports communications between one or more users of the computer device sickness reduction program 116 via the user computing devices 110 and 120, the server 140, and the communication network 102. In general, the application 122 is a platform in which users can manually activate the sickness reduction program 116 as well as report feedback on the effectiveness of the techniques applied by the sickness reduction program 116. The application 122 is also capable of processing input data from monitoring units 114A and 114B.

Server 140 includes a database 112B and is a device that is capable of communicating with the program device 110 and the user input device 120 via the communications network 102. As will be discussed with reference to FIG. 3, the server 140 may include internal components 902a and external components 904a, respectively. The server 140 may also operate in a cloud computing service model, such as Software as a Service (SaaS), Analytics as a Service (AaaS), Platform as a Service (PaaS), or Infrastructure as a Service (IaaS). The server 140 may also be located in a cloud computing deployment model, such as a private cloud, community cloud, public cloud, or hybrid cloud.

In the example embodiment, the database 112B is a collection of files including, but not limited to, HTML files, CSS files, XML files, and JavaScript files. In general, the database 112B is comprised of techniques suggested by a crowd-casted knowledge base, as well as techniques suggested to be effective in reducing motion sickness from researched medical data. In the example embodiment, the data can be transferred to the program device 110 and the user input device 120 via the communication network 102.

According to the present embodiment, a user using a program device 110 or a user input device 120 may use the sickness reduction program 116 to reduce the time the user experiences a motion sickness event. The sickness reduction method is explained in more detail below with respect to FIG. 2.

Figure 2:
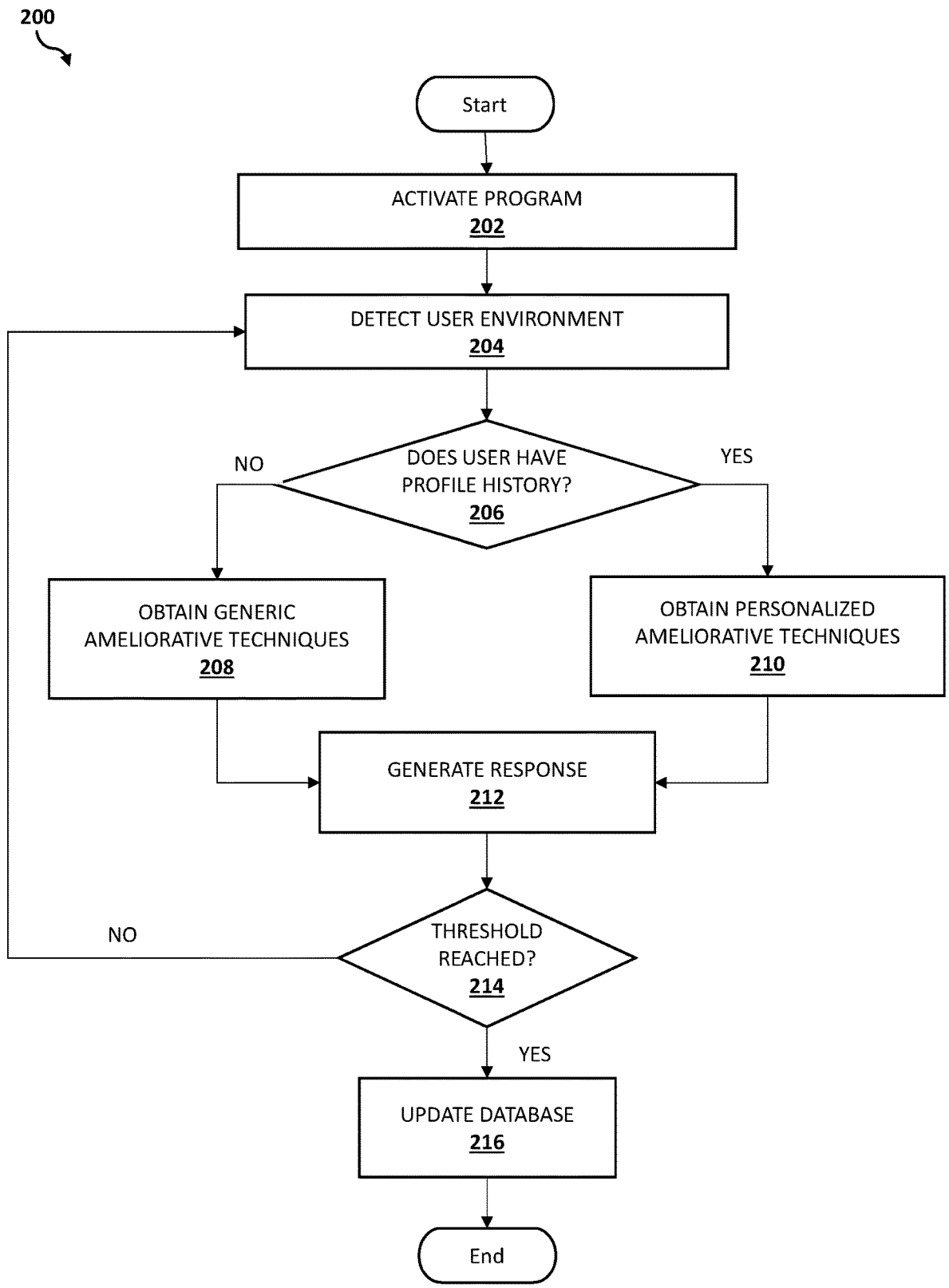
FIG. 2 depicts a flowchart illustrating the operations of sickness reduction program of the sickness reduction system in reducing the user's sense of motion sickness, in accordance with an embodiment of the present invention.

Referring now to FIG. 2, an operational flowchart illustrating the exemplary sickness reduction process 200 used by the sickness reduction program 116 according to at least one embodiment is depicted.

At 202, the sickness reduction program 116 is activated. Utilizing a program device 110, the sickness reduction program 116 may receive an input or alert that the user is experiencing or will experience a motion sickness event. In the example embodiment, the sickness reduction program 116 is activated automatically. Automatic activation may include activation of the sickness reduction program 116 without any user interaction of the program device 110, the user input device 120, or the server 140. In the example embodiment, the monitoring unit 114A (and the monitoring unit 114B) may use augmented reality (AR) device detection of biometric information associated with one or more Internet of Things (IoT) devices and sensors with context to trigger a response of the sickness reduction program 116. The monitoring unit 114A, 114B may detect heartbeat via a biometric sensor associated with a wearable device (e.g., watch), may detect eye gaze and blink rate via a biometric sensor associated with a wearable device (e.g., AR headset or AR glasses).

In at least one embodiment, the sickness reduction program 116 may be activated if the physiological state of the user detected by the monitoring unit 114A, 114B exceeds a threshold. Thresholds may be defined as the magnitude or intensity that should be exceeded (e.g., a reduction of symptoms by at least 50%, any reduction of symptoms, a reduction of nausea by 25% regardless of other symptoms) for a certain reaction, result, or condition to occur (e.g., for the sickness reduction program 116 to terminate). The threshold may be defined automatically by a machine learning (ML) algorithm that is trained from previously used data stored locally, in the database 112A or remotely, in the database 112B. Machine learning algorithms may utilize techniques, such as classification or regression, to infer with some level of confidence that the probability that such input (e.g. the physiological state of the user) has exceeded such defined threshold. Based on historical data associated with a specific user, a group of users, or a general population, the ML algorithm may analyze the data associated with the current motion sickness event (e.g., symptoms, information associated with the specific user) with the historical data (e.g., symptoms, information associated with the users or population associated with historical data) to predict or determine the likelihood that a technique may be successful with the specific user. In other embodiments, the predefined threshold may be predefined manually by the user, a representative of the user, a caretaker, a doctor, or a nurse. In other embodiments, the sickness reduction program 116 may be activated if the user's physiological state detected by the monitoring unit 114A, 114B shows any difference from the user's normal physiological state.

In further embodiments, the sickness reduction program 116 may be activated automatically through auditory capture of the user. For example, the monitoring unit 114A, 114B detects that the user said, "I think I'm going to be sick". After utilizing speech processing (e.g., natural language processing (NLP)) to understand the user's status, the sickness reduction program 116 may be activated. In even further embodiments, the monitoring units 114A, 114B may activate the sickness reduction program 116 by receiving information about the context (e.g., the general location of the user) and comparing such information to historically identified motion sickness engaging events (i.e., motion sickness events). Historically identified motion sickness engaging events may include flights, amusement park trips, boat activities, car rides, and water activities (e.g., scuba diving). Contextual information, in such embodiments, may be derived from visually processed cues by the monitoring units 114A, 114B. In other embodiments, contextual information, may be derived from information associated with the user's device. For example, if User A experiences motion sickness on a boat, then the sickness reduction program 116 is activated when the global positioning system (GPS) associated with User A's smart phone detects that User A is located in a lake.

In at least one embodiment, the sickness reduction program 116 may be activated manually by the user. Manual activation may include the start of an application on the program device 110 or the user input device 120, the push of a button on the program device 110 or the user input device 120, the flip of a switch on the program device 110 or the user input device 120, the search of motion sickness reduction techniques on the program device 110 or the user input device 120, the voice commands received by the program device 110 or the user input device 120, or the opening of the program device 110 or the user input device 120.

In at least one embodiment, the sickness reduction program 116 may be activated locally without a network connection. In such an embodiment, the monitoring unit 114A on the program device 110 may automatically detect the user's abnormal physiological state and activate the sickness reduction program 116, located on the same program device 110 without any transfer of information through the communication network 102. For example, the AR headset of the user determines that the heartbeat of User A is greater than the threshold and the sickness reduction program 116 should be activated.

In the present embodiment, the user may also manually activate the sickness reduction program 116 by inputting data on the program device 110 in ways previously enumerated. For example, the User A may push a button on the AR headset that activates the program directly, without network connection.

In further embodiments, the sickness reduction program 116 may be activated remotely, utilizing a network connection. In such embodiments, the monitoring unit 114B on the user input device 120 may automatically detect the user's abnormal physiological state and activate the sickness reduction program 116 through transfer of data via the communication network 102 to the program device 110 where the sickness reduction program 116 is located. For example, the User A's smart watch detects the heartbeat of User A is greater than the threshold. This information of the heightened heartbeat is sent to the AR headset to activate the program via the communication network 102. In such embodiments, where the sickness reduction program 116 may be activated remotely, the user may also manually activate the sickness reduction program 116 by inputting data on the user input device 120 in ways previously enumerated. For example, the User A may activate the sickness reduction program 116 remotely by opening an application on User A's mobile device that will send information to the AR headset via the communication network 102.

For example, a User B is on a cruise boat wearing AR glasses. Upon beginning to feel motion sick, User B says "I am starting to feel ill. These birds flying around me are not helping". With biometric sensors, the sickness reduction program recognizes User B is very nauseous, very sleepy, has a very high heart rate, and is very sweaty. The sickness reduction program of the AR glasses is now activated.

Next, at 204, the environment of the user is detected. The sickness reduction program 116 may collect data regarding the surroundings of the user and may detect components that may be triggering the motion sickness event.

The data collected about the environment of the user (i.e., user environment) may include the non-relative static positioned objects, or any non-relative non-static positioned objects, the presence of motion, the vehicle in which the user is located, the geographical position of the user, the weather (both in present time and what is predicted for the future), the time of day, the average color scheme of the environment (e.g., green may indicate trees, blue may indicate water), and the horizon in the user's visual field.

The sickness reduction program 116 may utilize the monitoring unit 114A, 114B to automatically collect data about the user environment. In such embodiment, the monitoring units 114A, 114B used may include biometric sensors, auditory detectors, motion sensors, cameras, global positioning systems (GPS), barometers, gyroscopes, magnetometers or accelerometers. In at least one embodiment, data may be obtained locally from the monitoring unit 114A, without the use of the communication network 102. In other embodiments, data may be obtained remotely from the monitoring unit 114B on the user input device 120 via the communication network 102.

In further embodiments, the sickness reduction program 116 may manually collect data about the user environment. In at least one embodiment, the user may utilize the local program device 110 to input information. Inputting information may use a graphical user interface (i.e. GUI) to allow a user to press a button, slide a bar across a scale (e.g., selecting a user location on a displayed map as such in the lake), select an option from a list (e.g., boat from "What type of vehicle are you on? 1. Boat 2. Plane 3. Car 4. other") or flip a switch (e.g., on land/off land). For example, the User A may indicate that User A is currently on a cruise boat that is currently docked. In another embodiment, the user may utilize the remote user input device 120 via the communication network 102. In such embodiment, the user may input data using the application 122 in which the users may verbally transmit information, type out information, twist a dial, or press a button.

In general, data may be collected to assist the sickness reduction program 116 in determining the overall user environment. Beyond collecting the data, the sickness reduction program 116, in at least one embodiment, may also analyze the data. In such embodiment, the sickness reduction program 116 may utilize automatic techniques such as natural language processing (NLP), image recognition, and digital image processing.

In at least one embodiment, data obtained may be stored long term and linked to the initial physiological state of the user that activated the program in the specific user profile history. Long term data storage and linkage to the user profile history may be beneficial to the sickness reduction program 116 by providing more data about the experience of the user (i.e., user experience) during the motion sickness event. For example, on Monday, User A may be experiencing a motion sickness event on a boat. On Wednesday, User A may be experiencing a motion sickness event on a plane. On Friday, User A may be experiencing a motion sickness event again on a boat. Having data stored about the environment during a specific motion sickness event may allow the sickness reduction program 116 to value the effective technique that was used on Monday over the effective technique that was used on Wednesday.

In other embodiments, the data obtained may be stored temporarily. Temporary storage may save space on the program device 110, the user input device 120, or the server 140.

In one embodiment, the sickness reduction program 116 may store user environment data in the local database 112A on the program device 110. In other embodiments, the sickness reduction program 116 may store user environment data in the remote database 112B on the server 140, where such data is transferred via the communication network 102.

In the present embodiment, the sickness reduction program 116 may be include an opt-in/opt-out feature in which the user may select to opt in or opt-out from the collection of data associated with the specific user. The opt-in/opt-out feature may be changed at any time, and if the user opts in to the sickness reduction program 116, then the user may be notified when the data collection has commenced. In some embodiments, the user may limit when data is collected, how the data is collected, what type of data is collected and the purposes for which the data collected is utilized. The user may also limit how and where the data is stored.

Continuing the previous example, User B's AR glasses utilize a camera and further, image analysis capabilities of the sickness reduction program 116 to scan the environment of the user to determine that User B is on a boat with strong waves and lots of flying birds.

Then, at 206, the sickness reduction program 116 determines whether the user has a profile history. Profile history of a user may include the user's name, age, gender, weight, height, address, places of interest that may trigger the sickness reduction program 116, previously used techniques that were effective, previously used techniques that were ineffective, previously identified triggering user environments (e.g., a boat), specific patterns or color overlays that were effective for the user (e.g., 30% increase of the blue spectrum in the visual field), specific objects for injection for a focal point that were effective for the user (e.g., a lighthouse), the most effective degree of amelioration for the user, the context in which each effective technique was used, and the average length of time of the motion sickness event for such user. A profile history may allow the sickness reduction program 116 to link the data collected from the activation of the sickness reduction program 116 to the user of the device (i.e., user device) during such triggering event, or environment to create more accurate and personalized future applications.

In at least one embodiment, the sickness reduction program 116 may analyze the local database 112A to search for a profile history associated with the user. In other embodiments, the sickness reduction program 116 may analyze the remote database 112B to search for a profile associated with the user.

In some embodiments, a profile history for a user (i.e., user profile history) may be initially created after the user's initial use of the sickness reduction program 116. Data regarding effective techniques and ineffective techniques as well as the measured length of time used to reduce the motion sickness of the user may be obtained from the sickness reduction program 116 via automatic feedback from the program device 110 or the user input device 120. In other embodiments, such data can be obtained via manual feedback from the program device 110 or the user input device 120.

In at least one embodiment, the sickness reduction program 116 may automatically link information to the user. In some embodiments, links may be defined by unique ID numbers, usernames, symbols, or any combination thereof.

In other embodiments, the sickness reduction program 116 may allow the user to manually input information. In such embodiments, the sickness reduction program 116 may detect the user is no longer experiencing a motion sickness event thereby warranting the deactivation of the sickness reduction program 116 and, by utilizing the local program device 110, may prompt the user to save the data recently obtained to a new profile where the user's personal information is stored. In other embodiments, the sickness reduction program 116 may detect the user is no longer experiencing a motion sickness event thereby warranting the deactivation of the sickness reduction program 116 and utilizing the remote user input device 120, may prompt the user to save the data recently obtained to a new profile, where the user's personal information is stored.

In at least one embodiment, personal information of the user may automatically be collected locally using auditory capture via biometric scanning, as seen in step 202. In another embodiment, personal information may automatically be input to the profile history using recognized personal data from remotely connected devices such as a mobile phone, a smart watch, or a laptop, where data is transferred across the communication network 102. In further embodiments, personal information may be input via user interaction with an interface to the profile history via manual input on the local program device 110. In some embodiments, personal information may be input to the profile history via user interaction with an interface to the profile history via manual input on a remotely connected device, the user input device 120.

In at least one embodiment, the profile history may be stored on the database 112A, relatively local to the sickness reduction program 116. In other embodiments, the profile history may be stored on the database 112B, relatively remote to the sickness reduction program 116.

If the sickness reduction program determines that the user does not have user profile history at 206 (i.e., decision 206 "NO" branch), generic ameliorative techniques are obtained at 208. Generic techniques (i.e., generic ameliorative techniques) may include methods that were effective for reducing motion sickness in the general population. Generic techniques may include the generation of a focal point object utilizing augmented reality, the use of a specific color scheme, the obfuscation of objects of a specific size, type, color, or path of motion, in addition to the modifications of the AR device itself (e.g., vibrations of the device, sounds generated by the device). In at least one embodiment, the sickness reduction program 116 may obtain techniques from the database 112A of the program device 110, where data can be obtained locally without the use of a network connection. In other embodiments, the sickness reduction program 116 may obtain techniques from the database 112B of the server 140 via the communication network 102. The database 112A, 112B, in embodiments, may be comprised of generic techniques in addition to coded methods of application. The database 112A, 112B may receive automatic input from medical research into effective motion sickness reduction techniques. For example, the sickness reduction program 116 may obtain a medical publication regarding motion sickness reduction techniques. Such generic techniques may be extracted from the medical publication and further, coded and added to the database 112A, 112B.

In other embodiments, the database 112A, 112B may receive automatic input from a crowdsourced knowledge base. In such embodiment, the crowdsourced knowledge base may include specific ameliorative techniques that were effective for other users of the sickness reduction program 116. The effectiveness of the technique may be determined by the length of time of the motion sickness event. For example, a technique that reduces the motion sickness of the User A to 20 minutes may be considered more effective than a technique that reduces the motion sickness of the User A to 40 minutes.

In other embodiments, the effectiveness of the technique (generic or specific) may be determined by the popularity of such technique. For example, a technique (generic or specific) that reduces the motion sickness of 50% of the users of the program device 110 may be considered more effective than a technique that reduces the motion sickness in 25% of the users.

If, however, the sickness reduction program 116 determines the user does have a user profile history at 206 (i.e., decision 206 "YES" branch), personalized ameliorative techniques (i.e. specific techniques) are obtained at 210. Specific techniques may include methods that were effective for the specific user of the sickness reduction program 116 in the current time. In some embodiments, specific techniques may include the collection of generic techniques with specific adjustments made to optimize the user experience of the sickness reduction program 116.

In at least one embodiment, as previously described, the effectiveness of the technique (generic or specific) may be determined by the length of time of the motion sickness event. In other embodiments, the effectiveness of the technique may be determined by the popularity of such technique by the specific user. For example, the User A uses a blue striped overlay 50% of the time and a red dotted overlay 10% of the time. As such, the blue striped overlay may be considered more effective.

In at least one embodiment, specific techniques may include generic techniques in combination with additional code that allows the sickness reduction program 116 to modify the specific pattern or color overlay of the user's visual field, the specific object that may be injected for a focal point in the user's visual field, and the specific degree of amelioration optimized to the user's sensitivity to the stimuli. For example, the sickness reduction program 116 may detect that User A has a user profile history that commands the sickness reduction program 116 to overlay the visual field of User A with a blue striped pattern. In such example, had the User A not had a user profile history, the sickness reduction program 116 may have commanded the AR device of the user to overlay the visual field of User A with a red dotted pattern utilizing the amelioration capabilities of the sickness reduction program 116, a pattern that may not have been as effective for the user. In general, the specifications of the user profile history may become more personalized with more feedback from the sickness reduction program 116, where the feedback is obtained from merely more uses of the sickness reduction program 116.

In at least embodiment, where the profile user history is stored on the local database 112A, the sickness reduction program 116 may obtain specific techniques by following the link between the discovered user profile history and the specific techniques in the database 112A. In other embodiments, where the profile user history is stored on a remote database 112B, the sickness reduction program 116 may obtain specific techniques by following the link between the discovered user profile and the specific techniques in the database 112B on the server 140 via the communication network 102.

Continuing the previous example, the sickness reduction program 116 has identified a profile history for User B. In such profile history, the sickness reduction program 116 identifies the user had been on a boat just a week prior experiencing the same symptoms. Last week, the sickness reduction program 116, utilizing the AR glasses, superimposed a lighthouse onto the horizon of User B. The sickness reduction program 116 is able to identify the same location and obtains the method of application for such specific technique. Additionally, after detecting the environment, the sickness reduction program 116 proposes obfuscation of the surrounding birds.

Then, at 212, a response is generated. In at least one embodiment, the sickness reduction program 116 may analyze the previously collected environment data and implement one of the previously collected techniques (i.e. general technique) based on the collected environment data. General techniques may be, in the example embodiment, a specific technique where the user has a profile history or a generic technique where the user does not have a profile history. For example, the sickness reduction program 116 collects a generic technique to instruct the AR device to overlay a blue spectrum onto the visual field of User A, when User A is on a boat. After the data within the database 112A, 112B from previous uses of the sickness reduction program 116 has been processed, the sickness reduction program 116 may determine such technique were effective when the user is on land. As such, the sickness reduction program 116 may analyze the stored history of the generic technique collected and process the environment data to understand that such generic technique is not currently fit for the user.

In other embodiments, the sickness reduction program 116 may implement the general technique previously collected without processing the environmental data. In such embodiments, the environmental data may be linked to the results of the technique implementation.

In at least one embodiment, the sickness reduction program 116 may automatically implement the technique. In such embodiment, the sickness reduction program 116 may detect a technique has been prompted for implementation after the collection of environmental data.

In other embodiments, the sickness reduction program 116 may implement the technique upon manual input. In general, manual input may include auditory commands, the use of the program device 110, 120 components (i.e. a keyboard to type a response), the pressing of a button, or the swiping of a display screen. In such embodiments, where the implementation of the technique depends on manual input, the sickness reduction program 116 may display to the user the technique that has been prompted for implementation. The sickness reduction program 116 may allow the user to accept, deny, or change the prompted technique. User input may occur locally, on the program device 110, via the display of the device (i.e. a display screen projected onto the visual field of the user). In other embodiments, user input may occur remotely, on the user input device 120, where the user utilizes the application 122 to accept, deny, or change the prompted technique.

Continuing the previous example, the sickness reduction program 116 applies the obfuscation of birds and the superimposition of a lighthouse onto the horizon of the visual field of User B.

Then, at 214, the sickness reduction program 116 determines whether a threshold has been reached. In the example embodiment, the sickness reduction program 116 may collect user physiological data subsequent to the implementation of a technique. User physiological data may be collected automatically. In such embodiments, the sickness reduction program 116 may utilize the monitoring unit 114A, 114B to detect heartbeat via biometric sensors associated with a wearable device (i.e. watch), eye gaze and blink rate detection via a biometric sensor associated with a wearable device (i.e. AR headset or AR glasses), sleepiness, nausea, or breathing patterns. In such embodiments, the sickness reduction program 116 may collect user physiological data locally with the monitoring unit 114A on the program device 110. In other embodiments, the sickness reduction program 116 collect user physiological data remotely with the monitoring unit 114B on the user input device 120 via communication network 102.

In further embodiments, user physiological data may be collected manually. Manual collection of data may include auditory inputs (i.e. "I feel less nauseous"), the use of the program device 110, 120 components (i.e. a keyboard to type a response), the pressing of a button, or the swiping of a display screen. In such embodiments, where data is collected manually, the sickness reduction program 116 may collect data locally using the program device 110. In other embodiments, the sickness reduction program 116 may collect data remotely using the user input device 120 via the communication network 102.

In at least one embodiment, the sickness reduction program 116 may analyze the collected data against the user's initial physiological data, collected at 202, and determines whether the collected data has reached the threshold. Thresholds may be defined as the magnitude or intensity that should be exceeded (e.g., a reduction of symptoms by at least 50%, any reduction of symptoms, a reduction of nausea by 25% regardless of other symptoms) for a certain reaction, result, or condition to occur (e.g., ending the sickness reduction program 116).

Such threshold, in at least one embodiment, may manually be defined by the user upon activation of the sickness reduction program 116. In other embodiments, the sickness reduction program 116, upon determining the user has a user profile history, define the threshold with previously used user thresholds. In further embodiments, the threshold may be predefined by a medical professional, caretaker, or relative of the user.

If the sickness reduction program 116 determines the threshold is reached at 214 (i.e., decision 214 "YES" branch), the sickness reduction program 116, at 216, updates the database. In at least one embodiment, the sickness reduction program 116 may first measure the length of time used to reduce the motion sickness of the user. In some embodiments, this length of time may include the difference in time between the activation of the sickness reduction program 116 and the deactivation of the sickness reduction program 116.

Subsequent to the measurement of time, the sickness reduction program 116 may update the database 112A, 112B. In at least one embodiment, the sickness reduction program 116 may send activation information to the database 112A, 112B. Activation information may include the user's initial physiological state, presence of a user profile history prior to implementation (e.g., YES or NO), the technique implemented, the environmental data collected, the user's final physiological state, the threshold used to deactivate the sickness reduction program 116 and the measured length of time used to reduce the motion sickness of the user during that activation of the sickness reduction program 116.

In at least one embodiment, the sickness reduction program 116 may transfer the activation information to the database 112A, 112B to update the user profile history. In some embodiments, if a user profile history has been previously identified, the sickness reduction program 116 may link the activation information to the user profile history in the database 112A, 112B. In other embodiments, if a user profile history has not been previously identified, the sickness reduction program 116 may create a user profile history for the user of the program device 110, as previously described in step 206. The sickness reduction program 116 may, then, link the activation information to the new user profile history in the database 112A, 112B.

In another embodiment, the sickness reduction program 116 may transfer the activation information to the database 112A, 112B to update the crowdsourced knowledge base. In this embodiment, activation information may be stored anonymously. In other embodiments, activation information may be stored in combination with user profile history information (e.g., age, gender, weight, height) for more accurate future technique suggestions upon future activation of the sickness reduction program 116.

In general, if the sickness reduction program 116 is commanded to stop at any time during the process of the sickness reduction program 116, the sickness reduction program 116 may progress to step 216 to update the database 112A, 112B with the activation information collected up to the point in which the sickness reduction program 116 was terminated. The sickness reduction program 116 may include an alert with the activation information to inform the sickness reduction program 116 upon future applications that such information was collected, however, may not be complete or may result in inaccurate future predictions.

Continuing the previous example, the sickness reduction program 116 determines User B to be less nauseous, still sleepy, but determines User B's heart rate has dropped significantly. In the profile history of User B, the sickness reduction program 116 identifies User B to have set a threshold of "any reduction in symptoms". Since User B's heart rate dropped and User B feels less nauseous, the sickness reduction program 116 determines the threshold has been reached. The sickness reduction program 116 then stops the implementation of the applied techniques and measures the motion sickness of User B to have decreased about 30 minutes of use. The profile history of User B is updated to include, "boat, obfuscation of birds, superimposition of light house, 30 minutes". Such data will provide the sickness reduction program 116 with more information to help determine the most effective technique when the User B experiences motion sickness again in the future.

If the sickness reduction program 116 determines the threshold is not reached at 214 (i.e., decision 214 "NO" branch), the sickness reduction program 116 returns to collect data at 204. The sickness reduction program 116 may then implement a new technique that may be more effective for the user of the program device 110. The sickness reduction program 116 may tag the activation information stored to that point as ineffective for the user in the specific context.

In at least one embodiment, if the sickness reduction program 116 consecutively tags activation information multiple times (e.g., default is five times) as ineffective, the sickness reduction program 116 may proceed to alert the user that the techniques implemented have not improved symptoms of motion sickness past the threshold. In such embodiment, the user may then have an option to allow for more ineffective tags (e.g., after 10 consecutive tags), manually select a technique to be implemented at 212, or deactivate the system at 216. In some embodiments, user input may be local from the program device 110, or remote, from the user input device 120.

The functionality of a computer may be improved by the sickness reduction program 116 because the sickness reduction program 116 may detect an environment that would trigger a motion sickness event for a specific user. By detecting the user's presence in such environment, the sickness reduction program 116 may be able to analyze data associated with such environment, such as surrounding non-static artifacts that may naturally enhance the symptoms of the user. Such data may allow the sickness reduction program 116 to introduce varying levels of stimuli, utilizing an augmented reality device, relative to a user's sensitivity to the stimuli, ability to adapt to the stimuli, and time factor of the user's response to the motion sickness. The sickness reduction program 116 may further advance current technology by dynamically removing, obfuscating, or changing the previously detected secondary artifacts. Additionally, the sickness reduction program 116 is capable of further advancing traditional methods by affixing proper contextual artifacts to the user's visual field using augmented reality.

It may be appreciated that FIG. 2 provides only an illustration of one embodiment and do not imply any limitations with regard to how different embodiments may be implemented. Many modifications to the depicted embodiment(s) may be made based on design and implementation requirements.

Figure 3:
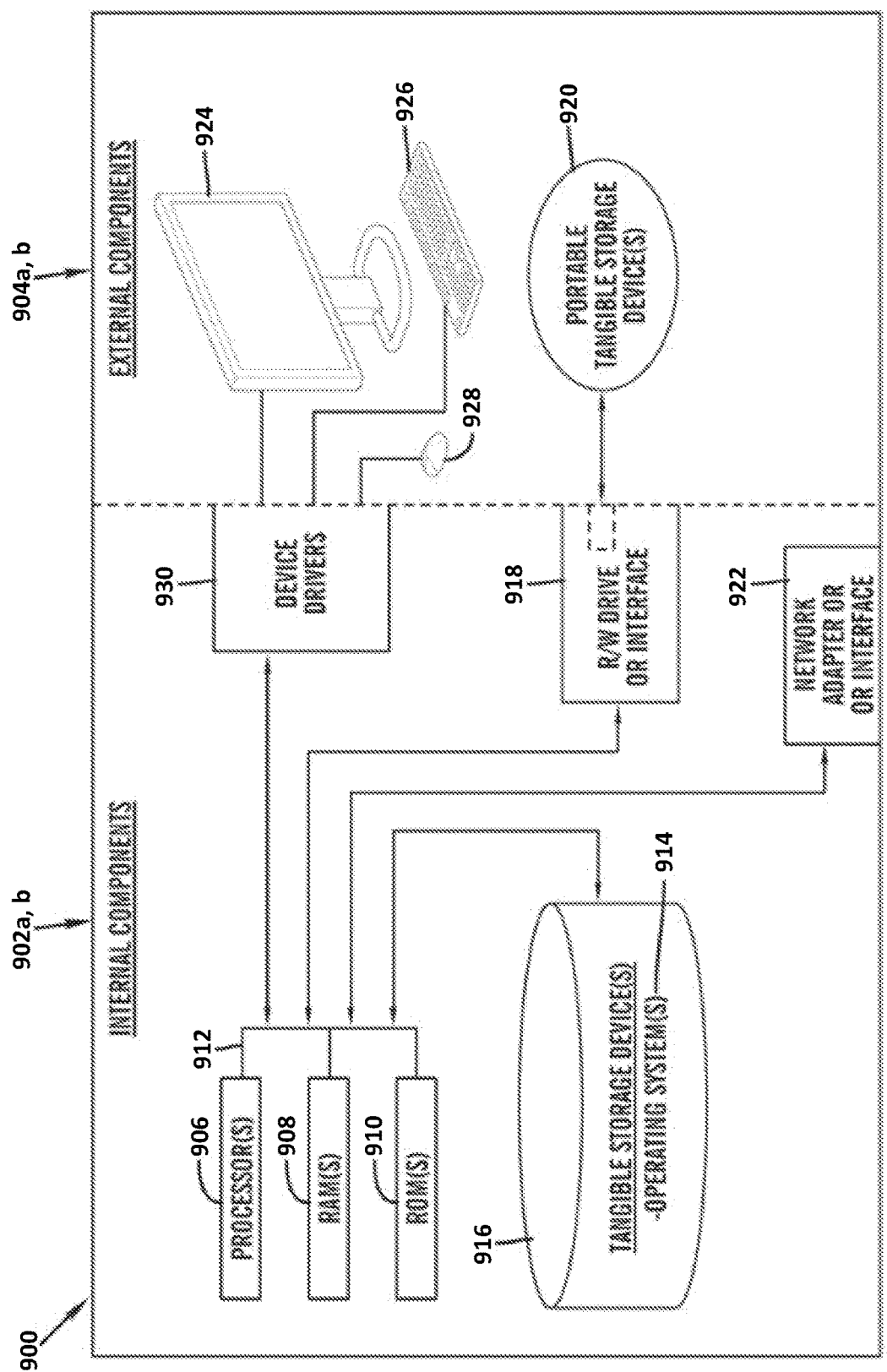
FIG. 3 depicts a block diagram depicting the hardware components of the sickness reduction system of FIG. 1, in accordance with an embodiment of the present invention.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The program device 110, the user input device 120, the server 140 and the communication network 102 may include respective sets of internal components 902 a, b and external components 904 a, b illustrated in FIG. 3. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the sickness reduction program 116, and the application 122 of the user input device 120, may be stored on one or more computer-readable tangible storage device 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the sickness reduction program 116 can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless wi-fi interface cards, or 3G or 4G wireless interface cards or other wired or wireless communication links. The sickness reduction program 116 of the program device 110 and the application 122 of the computing device 120 can be downloaded from an external computer (e.g., server) via a network (for example, the Internet, a local area network or other, wide area network) and respective network adapters or interfaces 922. From the network adapters (or switch port adaptors) or interfaces 922, the sickness reduction program 116 and the application 122 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
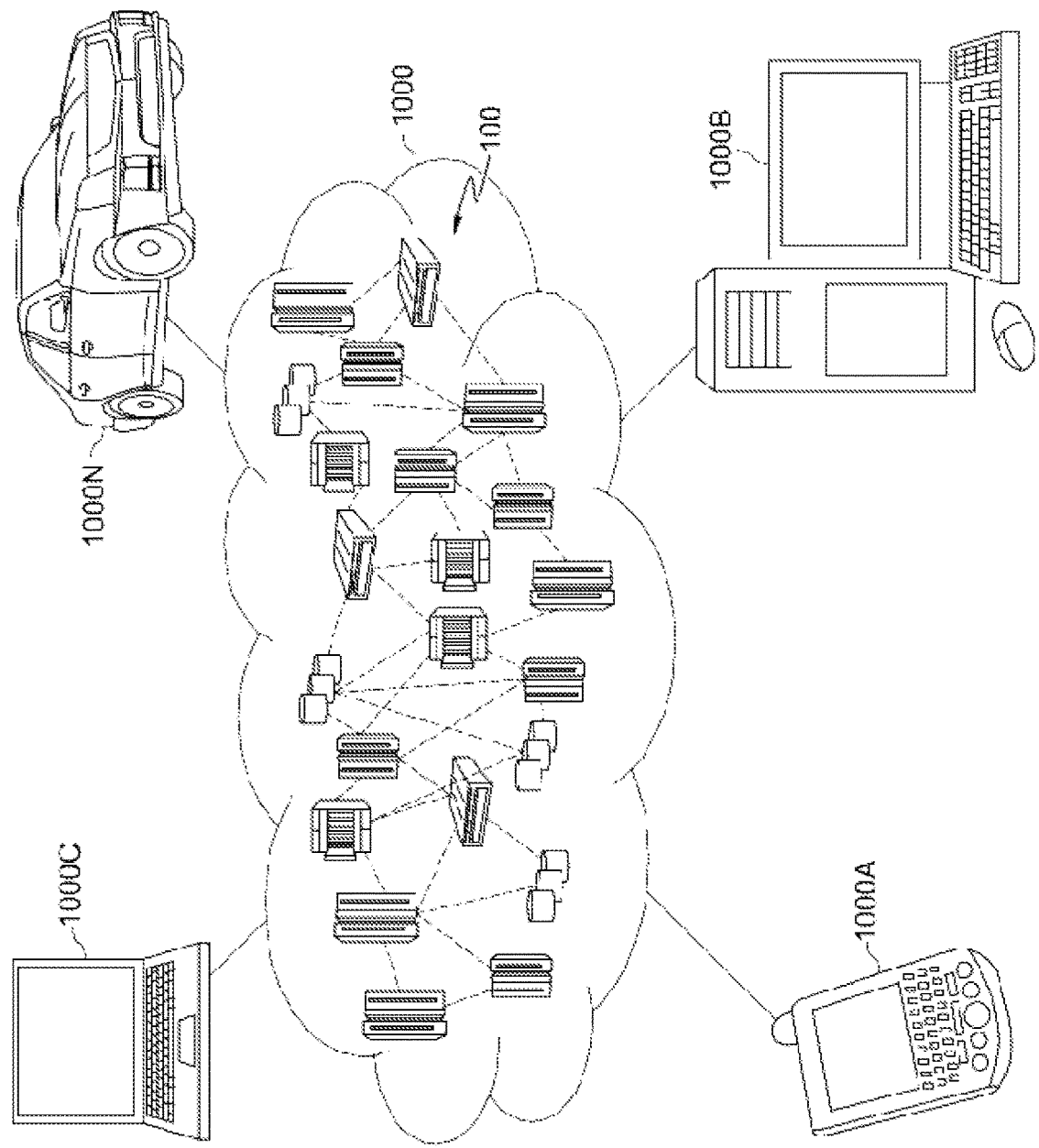
FIG. 4 depicts a cloud computing environment, in accordance with an embodiment of the present invention.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
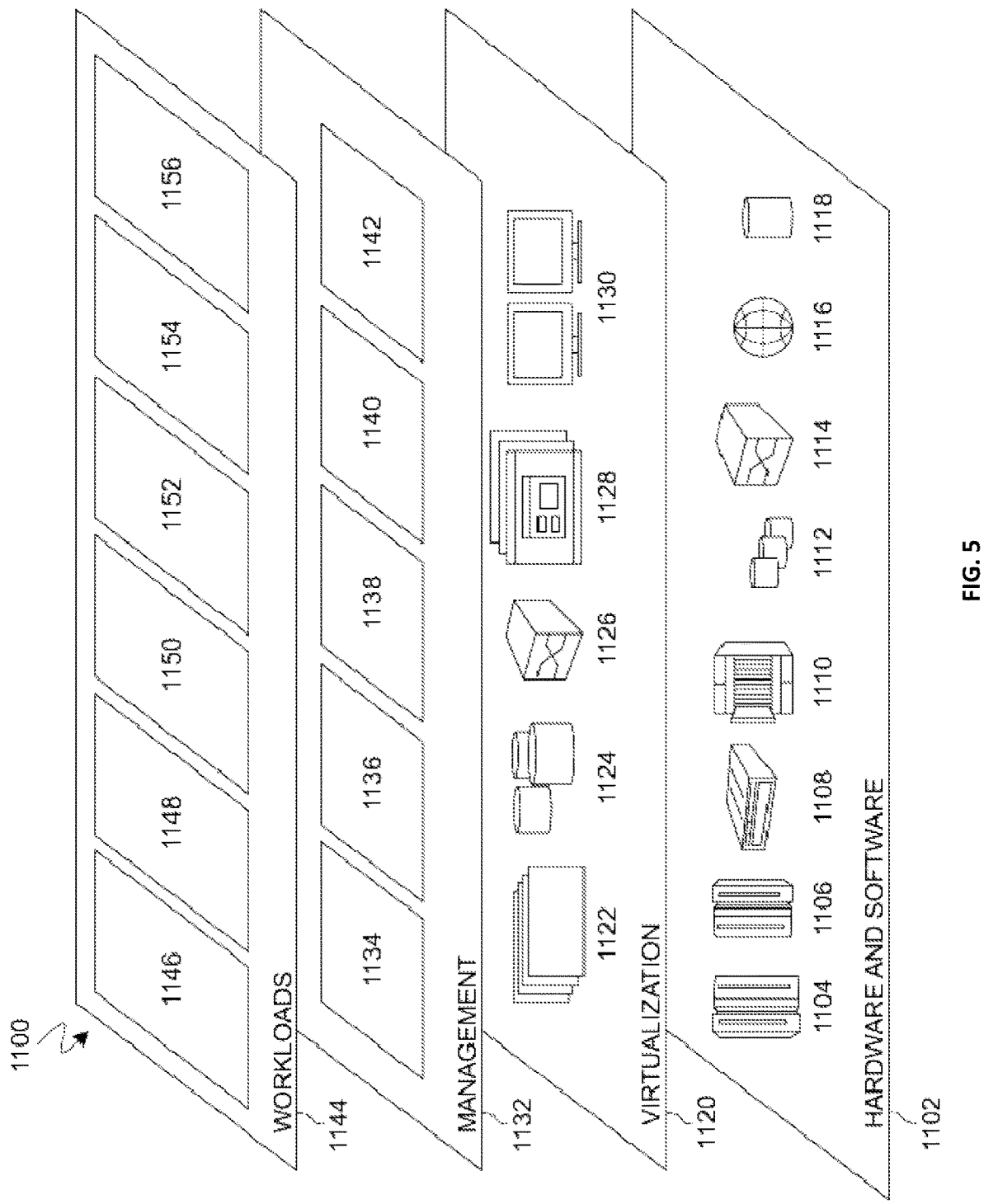
FIG. 5 depicts abstraction model layers, in accordance with an embodiment of the present invention.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 include hardware and software components. Examples of hardware components include: mainframes 1104; RISC (Reduced Instruction Set Computer) architecture-based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and sickness reduction program 1156.

The descriptions of the various embodiments of the present invention have been presented for purposes of illustration but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for reducing a motion sickness episode experienced by a user, the method comprising:

detecting a motion sickness triggering environment associated with the user, wherein detection of the triggering environment utilizes a plurality of analyzed data associated with a plurality of biometric and environmental sensors, the environmental sensors obtaining environmental data associated with an environment where the user is located;

extracting a piece of environmental data associated with the detected triggering environment in further association with the motion sickness episode experienced by the user;

generating one or more responses associated with the motion sickness episode experienced by the user based at least in-part upon the environmental data and the extracted piece of environmental data associated with the motion sickness episode, the one or more responses including one or more specific motion sickness ameliorative techniques most effective for the user from a user profile history, the user profile history including the one or more specific motion sickness ameliorative techniques most effective for the user;

implementing the generated one or more responses associated with the motion sickness episode by utilizing an augmented reality (AR) device to reduce an episode of motion sickness experienced by the user via the one or more specific motion sickness ameliorative techniques most effective for the user; and providing a piece of feedback associated with the generated one or more responses associated with the motion sickness episode, the piece of feedback including effectiveness of the one or more specific motion sickness ameliorative techniques most effective for the user.

2. The method of claim 1, wherein detecting the motion sickness triggering environment associated with the user, further comprises:

collecting a piece of data associated with a physiological state associated with the user; and analyzing the collected piece of data associated with the physiological state associated with the user.

3. The method of claim 2, wherein the analyzed piece of data associated with the physiological state of the user is selected from the group comprising:

(i) a heart rate;
(ii) a level of nausea;
(iii) a level of wakefulness;
(iv) a blood pressure rate;
(v) a level of eye gaze;
(vi) a blink rate; and
(vii) a rate associated with breathing patterns.

4. The method of claim 1, wherein extracting the piece of data associated with the detected motion sickness triggering environment in further association with the motion sickness episode experienced by the user, further comprises:

identifying the plurality of biometric and environmental sensors associated with the detected motion sickness triggering environment associated with the user.

5. The method of claim 1, wherein generating the one or more responses associated with the motion sickness episode experienced by the user, further comprises:

collecting the one or more specific motion sickness ameliorative techniques most effective for the user from the user profile history; and applying each of the one or more specific motion sickness ameliorative techniques most effective for the user from the collected one or more specific motion sickness ameliorative techniques most effective for the user.

6. The method of claim 1, wherein generating the one or more responses associated with the motion sickness episode experienced by the user, further comprises:

accessing a plurality of generic motion sickness techniques if the user does not have one or more specific motion sickness ameliorative techniques most effective for the user stored in the user profile history; and selecting, for applying to the user, one or more generic motion sickness techniques from the accessed plurality of generic motion sickness techniques based on a plurality of user data associated with a user stimuli sensitivity, a user stimuli history, and a response time factor associated with the user.

7. The method of claim 6, wherein the one or more generic techniques is selected from the group comprising:

(i) a generation of a focal point object associated with the AR device,
(ii) a use of specific color scheme in a visual field associated with the user,
(iii) a modification associated with a plurality of sights and a plurality of sounds associated with a perceived field of the user,
(iv) an obfuscation of a plurality of objects,
(v) a prompting of the user to modify a current position,
(vi) a simplification of a sensory input,
(vii) a reduction of pitch and roll associated with an identified horizon,
(viii) an alteration of a luminescence and a temperature warmth,
(ix) a detection and a guidance associated with a rate associated with a breathing pattern of the user,
(x) a modification of a current state of a device, and
(xi) a blockage of one or more non-static items moving non-relative to the AR device.

8. The method of claim 1, wherein providing the piece of feedback associated with the generated one or more responses associated with the motion sickness episode, further comprises:

measuring a length of time used to reduce the motion sickness of the user;

linking the piece of feedback to the user profile history of the user; and linking the piece of feedback to a crowdsourced knowledge base.

9. A computer system for reducing a motion sickness episode experienced by a user, comprising:

one or more processors, one or more computer-readable memories, one or more computer-readable tangible storage media, and program instructions stored on at least one of the one or more computer-readable tangible storage media for execution by at least one of the one or more processors via at least one of the one or more memories, wherein the computer system is configured to perform a method comprising:

detecting a motion sickness triggering environment associated with the user, wherein detection of the triggering environment utilizes a plurality of analyzed data associated with a plurality of biometric and environmental sensors, the environmental sensors obtaining environmental data associated with an environment where the user is located;

extracting a piece of environmental data associated with the detected triggering environment in further association with the motion sickness episode experienced by the user;

generating one or more responses associated with the motion sickness episode experienced by the user based at least in-part upon the environmental data and the extracted piece of environmental data associated with the motion sickness episode, the one or more responses including one or more specific motion sickness ameliorative techniques most effective for the user in a user profile history for the user, the user profile history including the one or more specific motion sickness ameliorative techniques most effective for the user;

implementing the generated one or more responses associated with the motion sickness episode by utilizing an augmented reality (AR) device to reduce an episode of motion sickness experienced by the user via the one or more specific motion sickness ameliorative techniques most effective for the user; and providing a piece of feedback associated with the generated one or more responses associated with the motion sickness episode, the piece of feedback including effectiveness of the one or more specific motion sickness ameliorative techniques most effective for the user.

10. The computer system of claim 9, wherein detecting the motion sickness triggering environment associated with the user, further comprises:

collecting a piece of data associated with a physiological state associated with the user; and analyzing the collected piece of data associated with the physiological state associated with the user.

11. The computer system of claim 10, wherein the analyzed piece of data associated with the physiological state of the user is selected from the group comprising:
(i) a heart rate;
(ii) a level of nausea;
(iii) a level of wakefulness;
(iv) a blood pressure rate;
(v) a level of eye gaze;
(vi) a blink rate; and
(vii) a rate associated with breathing patterns.

12. The computer system of claim 9, wherein extracting the piece of data associated with the detected motion sickness triggering environment in further association with the motion sickness episode experienced by the user, further comprises:

identifying the plurality of biometric and environmental sensors associated with the detected motion sickness triggering environment associated with the user.

13. The computer system of claim 9, wherein generating the one or more responses associated with the motion sickness episode experienced by the user, further comprises:

collecting the one or more specific motion sickness ameliorative techniques most effective for the user from the user profile history; and applying each of the one or more specific motion sickness ameliorative techniques most effective for the user from the collected one or more specific motion sickness ameliorative techniques most effective for the user.

14. The computer system of claim 9, wherein generating the one or more responses associated with the motion sickness episode experienced by the user, further comprises:

accessing a plurality of generic techniques if the user does not have one or more specific motion sickness ameliorative techniques most effective for the user stored in the user profile history; and selecting, for applying to the user, one or more generic motion sickness techniques from the accessed plurality of generic motion sickness techniques based on a plurality of user data associated with a user stimuli sensitivity, a user stimuli history, and a response time factor associated with the user.

15. The computer system of claim 14, wherein the one or more generic techniques is selected from the group comprising:
(i) a generation of a focal point object associated with the AR device,
(ii) a use of specific color scheme in a visual field associated with the user,
(iii) a modification associated with a plurality of sights and a plurality of sounds associated with a perceived field of the user,
(iv) an obfuscation of a plurality of objects,
(v) a prompting of the user to modify a current position,
(vi) a simplification of a sensory input,
(vii) a reduction of pitch and roll associated with an identified horizon,
(viii) an alteration of a luminescence and a temperature warmth,
(ix) a detection and a guidance associated with a rate associated with a breathing pattern of the user,
(x) a modification of a current state of a device, and
(xi) a blockage of one or more non-static items moving non-relative to the AR device.

16. The computer system of claim 9, wherein providing the piece of feedback associated with the generated one or more responses associated with the motion sickness episode, further comprises:

measuring a length of time used to reduce the motion sickness of the user, linking the piece of feedback to the user profile history of the user, and linking the piece of feedback to a crowdsourced knowledge base.

17. A computer program product for reducing a motion sickness episode experienced by a user, comprising:

one or more computer-readable tangible storage media and program instructions stored on at least one of the one or more computer-readable tangible storage media, the program instructions executable by a processor to cause the processor to perform a method comprising:

detecting a motion sickness triggering environment associated with the user, wherein detection of the triggering environment utilizes a plurality of analyzed data associated with a plurality of biometric and environmental sensors, the environmental sensors obtaining environmental data associated with an environment where the user is located;

extracting a piece of environmental data associated with the detected triggering environment in further association with the motion sickness episode experienced by the user;

generating one or more responses associated with the motion sickness episode experienced by the user based at least in-part upon the environmental data and the extracted piece of environmental data associated with the motion sickness episode, the one or more responses including one or more specific motion sickness ameliorative techniques most effective for the user from a user profile history, the user profile history including the one or more specific motion sickness ameliorative techniques most effective for the user;

implementing the generated one or more responses associated with the motion sickness episode by utilizing an augmented reality (AR) device to reduce an episode of motion sickness experienced by the user via the one or more specific motion sickness ameliorative techniques most effective for the user; and providing a piece of feedback associated with the generated one or more responses associated with the motion sickness episode, the piece of feedback including effectiveness of the one or more specific motion sickness ameliorative techniques most effective for the user.

18. The computer program product of claim 17, wherein detecting the motion sickness triggering environment associated with the user, further comprises:

collecting a piece of data associated with a physiological state associated with the user; and analyzing the collected piece of data associated with the physiological state associated with the user.

19. The computer program product of claim 18, wherein the analyzed piece of data associated with the physiological state of the user is selected from the group comprising:
(i) a heart rate;
(ii) a level of nausea;
(iii) a level of wakefulness;
(iv) a blood pressure rate;
(v) a level of eye gaze;
(vi) a blink rate; and
(vii) a rate associated with breathing patterns.

20. The computer program product of claim 17, wherein extracting the piece of data associated with the detected motion sickness triggering environment in further association with the motion sickness episode experienced by the user, further comprises:
  identifying the plurality of biometric and environmental sensors associated with the detected motion sickness triggering environment associated with the user.

* * * * *